US 9,251,122 B2

(12) United States Patent
Perenon et al.

(10) Patent No.: US 9,251,122 B2
(45) Date of Patent: Feb. 2, 2016

(54) METHOD AND APPARATUS FOR ESTIMATING A MOLECULAR MASS PARAMETER IN A SAMPLE

(75) Inventors: Rémi Perenon, Voiron (FR); Ali Mohammad-Djafari, Orsay (FR); Pierre Grangeat, Saint Ismier (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 684 days.

(21) Appl. No.: 13/603,716

(22) Filed: Sep. 5, 2012

(65) Prior Publication Data
US 2013/0238252 A1   Sep. 12, 2013

(30) Foreign Application Priority Data

Sep. 5, 2011   (FR) ..................................... 11 57857

(51) Int. Cl.
| | |
|---|---|
| *G01N 31/00* | (2006.01) |
| *G06F 17/18* | (2006.01) |
| *B82Y 15/00* | (2011.01) |
| *B82Y 35/00* | (2011.01) |
| *G01N 29/02* | (2006.01) |

(Continued)

(52) U.S. Cl.
CPC ................. G06F 17/18 (2013.01); B82Y 15/00 (2013.01); B82Y 35/00 (2013.01); G01N 29/022 (2013.01); G01N 29/30 (2013.01); G06F 19/703 (2013.01); H01J 49/0018 (2013.01); *G01N 2291/0255* (2013.01); *G01N 2291/0256* (2013.01); *G01N 2291/0427* (2013.01); *G06F 19/707* (2013.01)

(58) Field of Classification Search
None
See application file for complete search history.

(56) References Cited

U.S. PATENT DOCUMENTS

| | | | |
|---|---|---|---|
| 8,507,845 B2 * | 8/2013 | Blick et al. | ..................... 250/282 |
| 2007/0023621 A1 * | 2/2007 | Blick et al. | ..................... 250/251 |

(Continued)

FOREIGN PATENT DOCUMENTS

| | | |
|---|---|---|
| EP | 1 047 108 | 10/2000 |
| FR | 2 920 235 | 2/2009 |

OTHER PUBLICATIONS

Daniel Gruber, et al., "Counting of obscure events: A Bayesian approach", Chemical Physics Letters, vol. 474, No. 4-6, Jun. 4, 2009, pp. 371-374.

(Continued)

*Primary Examiner* — Aditya Bhat
(74) *Attorney, Agent, or Firm* — Oblon, McClelland, Maier & Neustadt, L.L.P.

(57) ABSTRACT

A method for estimating a molecular mass parameter in a sample that includes at least one component of given molecular mass, comprising the steps consisting of passing the sample through a processing chain comprising a mass spectrometer with a MEMS or NEMS electromechanical sensor, in this way obtaining a signal representing the molecular mass parameter and estimating the molecular mass parameter by means of a signal processing device. The molecular mass parameter is defined on the basis of a parameter of time distribution of successive detections, by the MEMS or NEMS electromechanical sensor, of the adsorption of said component, and the estimation of the molecular mass parameter is made by Bayesian inference, on the basis of a direct analytical modeling of said signal according to the molecular mass parameter and to technical parameters of the processing chain comprising at least one technical parameter of the MEMS or NEMS electromechanical sensor.

11 Claims, 3 Drawing Sheets

(51) Int. Cl.
  *G01N 29/30* (2006.01)
  *H01J 49/00* (2006.01)
  *G06F 19/00* (2011.01)

(56) References Cited

U.S. PATENT DOCUMENTS

2009/0055101 A1 2/2009 Strubel et al.
2009/0261241 A1 10/2009 Roukes et al.

OTHER PUBLICATIONS

T. Schwarz-Selinger, et al., "Analysis of multicomponent mass spectra applying Bayesian probability theory", Journal of Mass Spectrometry, vol. 36, Aug. 1, 2001, pp. 866-874.

French Preliminary Search Report and Written Opinion issued Apr. 24, 2012 in corresponding French Application No. 11 57857 filed on Sep. 5, 2011 (with an English Translation of Categories).

* cited by examiner

METHOD AND APPARATUS FOR ESTIMATING A MOLECULAR MASS PARAMETER IN A SAMPLE

The present invention relates to a method and a device for estimating a molecular mass parameter in a sample.

BACKGROUND OF THE INVENTION

A particularly promising application of such a method is for example the analysis of biological samples such as blood or plasma samples in order to extract therefrom biological parameters such as a mass spectrum estimation for revealing molecular concentrations of proteins. Knowledge of this mass spectrum and/or these concentrations makes it possible to detect abnormalities or illnesses. In particular, it is known that some illnesses such as cancers, even at an early stage, may have a possibly detectable impact on the molecular concentrations of certain proteins. The study of these proteins, referred to as proteomics, thus becomes an essential element in many fields in medicine. This is because proteins are particularly interesting cases of biomarkers that describe both the expression of genes and the influence of the environment and are more accessible in a good number of organic fluids (blood, serum, urine, biological fluid, lysate of a biological sample, etc). However, more generally, the analysis of samples for extracting relevant molecular mass parameters affording for example an aid to the diagnosis of a state (health, pollution, etc) that can be associated with these samples is a promising field of application of a method according to the invention.

Among the concrete applications that can be envisaged, the following may be noted: the biological analysis of samples by detecting proteins and their masses; the characterization of bacteria by mass spectrometry; the characterization of the state of pollution of a chemical sample (for example the analysis of a gas in an environment or the analysis a heavy metal in a liquid sample). The relevant parameters extracted may comprise mass spectra of components such as molecules (peptides, proteins, enzymes, antibodies, etc) or molecular assemblies. Molecular assembly means for example a nanoparticle or a biological species (bacterium, microorganism, cell, etc).

In the case of a biological analysis by detecting proteins, the entire difficulty is arriving at the most precise possible estimation in a noisy environment where the proteins of interest are sometimes present in the sample in very small quantities.

In general, the sample passes through a processing chain comprising at least a mass spectrometer. This processing chain is designed for the supply of a signal representing masses of components in the sample according to a mass/charge ratio in the mass spectrometer.

Optionally, the processing chain may comprise, upstream of the mass spectrometer, making it necessary for the sample to be in nebulized gaseous phase, a vaporizer and an electrospray (or equivalent, in order to carry out ionization and/or desorption of the components of the sample) able to proceed with the phase change necessary when the sample to be analyzed is for example available in liquid or solid phase.

Finally, when the mass spectrometer used has a MEMS (Micro Electro Mechanical System) or NEMS (Nano Electro Mechanical System) electromechanical sensor, the processing chain may optionally comprise focusing electronics, for example a hexapole, guiding the ionized components through a chamber at very low pressure. MEMS Sensors are used for compounds with high molecular masses, for example molecular assemblies, while NEMS sensors are used for detecting compounds with lower molecular masses, for example single molecules.

The major advantage of using a mass spectrometer with a MEMS or NEMS electromechanical sensor in the processing chain is to allow a quantification and estimation of the mass parameter (for example the mass or mass spectrum) at the level of the single component. The mass spectrometry task is then carried out in counting mode, which gives rise to great sensitivity and a reduction in the measurement noise.

DESCRIPTION OF THE PRIOR ART

One known method of estimating a molecular mass parameter in a sample using such a mass spectrometer with a MEMS or NEMS sensor is described in the article by Naik et al, entitled "Towards single-molecule nanomechanical mass spectrometry", published in Nature Nanotechnology, vol. 4, pages 445-450, July 2009. It comprises the following steps:
  passing the sample through a processing chain comprising a mass spectrometer with a MEMS of NEMS electromechanical sensor,
  obtaining thus a signal representing the molecular mass parameter according to at least one variable of the processing chain, and in particular the electromechanical sensor, and
  estimating the molecular mass parameter by means of a signal processing device.

In this document, the principle is more precisely as follows:
  molecules are vaporized and then ionized by electrospray,
  these ionized molecules are guided through a hexapole,
  the molecules are then bombarded on a NEMS sensor of the mass spectrometer,
  an electronic reading system reads certain characteristics of the sensor,
  a signal processing estimates the number of molecules upstream of the processing chain.

In concrete terms, the molecules are adsorbed on the NEMS sensor. This sensor, behaving as a mass-spring system, sees its resonant frequency fall as a function of the mass adsorbed. The electronic reading system, which is in this case a phase lock loop, reads this resonant frequency.

The signal processing proposed in this document is then carried out in accordance with the following steps:
  prior estimation of the standard deviation of the noise while not bombarding the NEMS sensor,
  detection of instants of adsorption of molecules bombarded on the NEMS sensor, numerically deriving the observed signal and keeping only the values of the derivative greater than twice the standard deviation estimated previously,
  estimating frequency drops at the instants previously detected via an estimation based on the least squares method,
  transforming the estimation of the frequency drops into an estimation of molecular masses.

This estimation method remains very experimental and approximate. In addition, it is carried out globally on all the frequency drops. There is no estimation molecule by molecule.

It may thus be wished to provide a method for estimating a molecular mass parameter that at least partly dispenses with the aforementioned problems and constraints and improves on the existing methods.

SUMMARY OF THE INVENTION

A method for estimating a molecular mass parameter in a sample that includes at least one component of a given molecular mass is therefore proposed, comprising the following steps:
passing the sample through a processing chain comprising a mass spectrometer with a MEMS or NEMS electromechanical sensor,
in this way obtaining a signal representing the molecular mass parameter, and
estimating the molecular mass parameter by means of a signal processing device,
wherein the estimation of the molecular mass parameter is made by Bayesian inference, on the basis of direct analytical modeling of said signal according to the molecular mass parameter and to technical parameters of the processing chain comprising at least one technical parameter of the electromechanical sensor.

Thus the analytical modeling proposed makes the statistically observed signal dependent on the mass parameter and on a set of technical parameters of the processing chain, some of which are directly related to the presence of a mass spectrometer with a MEMS or NEMS sensor. The knowledge, a priori incomplete, of some of these parameters can be modeled by probability laws, while others are obtained in a deterministic fashion, by learning or possibly by calibration of the processing chain. Inversion by Bayesian inference of the statistical model obtained then makes it possible to obtain a simple and reliable estimation of the molecular mass parameter in question, from the signal observed at the output of the processing chain.

Advantageously, the molecular mass parameter is defined on the basis of a parameter of time distribution of successive detections, by the MEMS or NEMS electromechanical sensor, of the adsorption of said component.

The mass of said component, or of each component included in the sample, can then be inferred, as well as the number of detections of said component.

Optionally, the analytical modeling comprises the definition of a parameter representing the instants, referred to as the detection instants, at which the electromechanical sensor detects the adsorption of said component. In that case, the molecular mass parameter is advantageously defined from said parameter that represents the detection instants Optionally also, the parameter representing the detection instants takes the form of a vector or of a list of parameters of each component detection.

Optionally also, a method as proposed may further comprise a step for detecting the adsorption sites of components on the MEMS or NEMS electromechanical sensor, and in that case the analytical modeling further comprises a parameter of time distribution of said adsorption sites and a deterministic function that returns a value of drop in frequency for each pair of values for a mass of adsorbed component and for a corresponding adsorption site.

Optionally also, at least two of the molecular mass and processing chain parameters according to which the direct analytical modeling of said signal is defined have a probabilistic dependency relationship with each other, and the signal processing by Bayesian inference is further carried out on the basis of a modeling by a conditional prior probability law of this dependency, Thus the modeling may be refined, and therefore approach reality, by integrating a hierarchy between signals or between signals and parameters by means of probabilistic dependencies translated by conditional probability laws, knowing that these probabilistic dependencies may be modeled a priori, for example either by specific learning, or by a realistic model imposed by experience. The result is finally a better estimation of the molecular mass parameter concerned.

Optionally also, the step of estimating the molecular mass parameter comprises, by approximation of the joint posterior probability law of a parameter linked to the molecular mass parameter and the technical parameters of the processing chain conditionally to the signal obtained by means of a stochastic sampling algorithm:
a loop for sampling these parameters, supplying sampled values of these parameters, and
an estimation of the molecular mass parameter calculated from the sampled values supplied.

Thus, on the basis of a knowledge of models of prior probability laws, conditional or not, of at least some of these parameters, it becomes possible to simply process the signal supplied by the processing chain in order to extract therefrom estimations of these parameters.

Optionally also:
the parameter representing the detection instants takes the form of a vector with binary components, one of the binary values, A, indicating the detection of an adsorption,
at each iteration of the sampling loop, a sample of this parameter is calculated in a neighborhood of the sample calculated at the previous iteration,
the neighborhood of a current sample of this parameter is defined as follows: any sample comprising a component with A plus or minus, a component with A shifted or a component A grouping together two components with successive As of the current sample.

Optionally also:
at each iteration of the sampling loop, a joint probability of at least all the sampled parameters is estimated, and
the estimation of the molecular mass parameter is made, conjointly with that of the sampled parameters, on the basis of the successive values of the said joint probability.

Optionally also, the molecular mass parameter is a mass spectrum relating to at least one component the mass of which forms part of the parameters processed by the sampling loop and is one of the elements of the set consisting of a single molecular mass, a discrete plurality of molecular masses and a continuous distribution of masses.

Optionally also, the molecular mass parameter relates to proteins and the sample comprises one of the elements of the set consisting of blood, plasma, urine, biological fluid and lysate of a biological sample.

Another subject matter of the invention is a device for estimating a molecular mass parameter in a sample, comprising:
a chain for processing the sample comprising a mass spectrometer with a MEMS or NEMS electromechanical sensor, designed for supplying a signal representing the molecular mass parameter,
a signal processing device designed to apply, in combination with the processing chain, a method for estimating a molecular mass parameter as defined previously.

BRIEF DESCRIPTION OF THE DRAWINGS

The invention will be better understood by means of the following description, given solely by way of example and made with reference to the accompanying drawings, in which.

DESCRIPTION OF THE PREFERRED EMBODIMENTS

Figure 1:
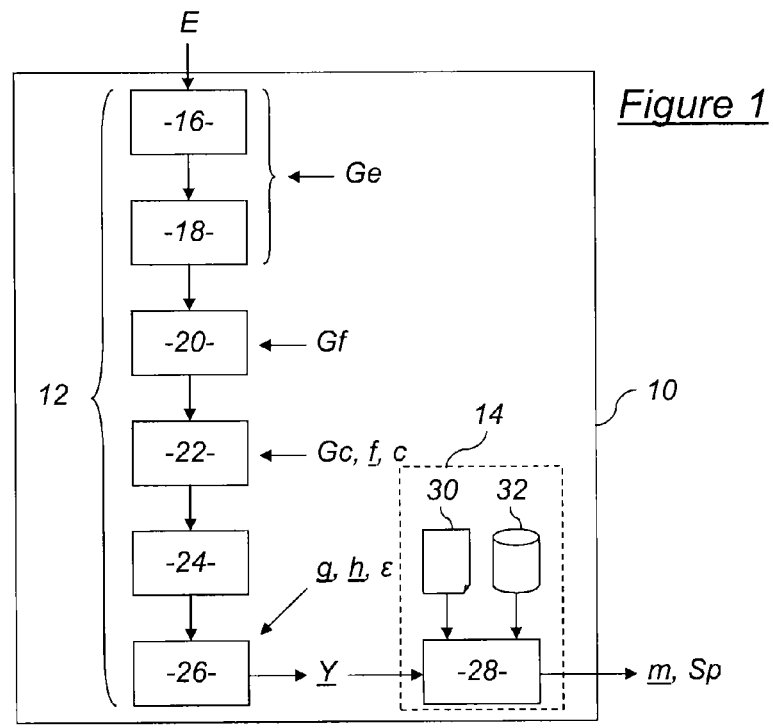
FIG. 1 shows schematically the general structure of a device for estimating a molecular mass parameter according to one embodiment of the invention.

The device 10 for estimating a molecular mass parameter in a sample E, shown schematically in FIG. 1, comprises a chain 12 for processing the sample E designed for supplying a signal Y representing this molecular mass parameter as a function of at least one variable of the processing chain 12. It also comprises a signal processing device 14 designed to apply, in combination with the processing chain 12, a method for estimating this molecular mass parameter according to the technical parameters of the processing chain 12.

In the example that will be detailed hereinafter but which must not be considered to be limitative, the estimated parameter is a mass spectrum relating to biological components of the sample E then considered as a biological sample, and the processing chain 12 is a biological processing chain. More precisely, the components are proteins of interest, for example selected according to their relevance for characterizing an abnormality, disease or illness, and the sample E is a sample of blood, plasma, urine, or any other biological fluid or a biological sample lysate.

In the biological processing chain 12, the sample E passes first of all through a source of ions, that is to say a vaporizer 16, and then an ionizer 18 (electrospray or equivalent), so as to be in nebulized gaseous phase. This source of ions 16, 18 has a gain Ge that may, according to a simplified model of the processing chain 12, be considered to be constant and independent of the mass of the molecules present in the sample E. This gain Ge can be termed a "certain" parameter in that it may be considered to be constant from one biological processing to another.

The sample E then passes through a focusing hexapole 20, guiding the ionized molecules through a chamber at very low pressure. This focusing also has a gain Gf that may, according to a simplified model of the processing chain 12, be considered to be constant and independent of the mass of the molecules present in the sample E. This gain Gf may also be termed a "certain" parameter.

Then the ionized molecules of the sample E encounter the MEMS or NEMS electromechanical sensor of a mass spectrometer 22, for example similar the one that is described in the aforementioned article by Naik et al. They are adsorbed by this sensor according to a gain Gc which may, according to a simplified model of the processing chain 12, be considered to be constant and independent of the mass of the molecules present in the sample E. This gain Gc may also be termed a "certain" parameter.

For each molecule adsorbed by the MEMS or NEMS sensor of the mass spectrometer 22, a drop in natural resonant frequency of the sensor can be observed, this drop in frequency being dependent on the place where the molecule was adsorbed on the sensor and its mass. This is because the natural resonant frequency of the sensor depends on its effective mass, which depends not only on the total mass but the distribution of mass along the sensor. In order better to parameterize the function that defines the dependency of the natural resonant frequency of the MEMS or NEMS sensor on the adsorption site and the adsorbed mass, the processing chain 12 may optionally comprise a device 24 for detecting the position of the last molecule adsorbed on the MEMS or NEMS sensor. It is considered that such a device 24 is known and will therefore not be detailed. Reference can in particular be made to the article by Dohn et al, entitled "Mass and position determination of attached particles on cantilever based mass sensors" published online in Review of Scientific Instruments 78, 103303, 31 Oct. 2007.

According to a variant, the MEMS or NEMS sensor is functionalized locally, which makes it possible to predetermine the position of any adsorption. The functionalization can be carried out on a sufficiently narrow area, so that the variability of the absorption site has no influence on the measurement.

Finally, the processing chain 12 comprises a system 26 for electronic reading of the frequency drops of the MEMS or NEMS sensor of the mass spectrometer 22 in order to supply an observed signal Y that then represents the molecular masses of the proteins in the sample E. This signal Y corresponds to the recording of the instantaneous resonant frequency of the MEMS or NEMS sensor as a function of time.

In order to determine the "certain" parameters and other constants of the processing chain, the latter may be calibrated.

A first type of calibration, referred to external calibration, can be carried out by means of a sample $E_{CALIB}$ of external calibration components the molecular profile of which is known, for example a sample of standard proteins or predetermined proteins contained in cocktails of proteins, the molecular mass of these calibration proteins being known and their concentration (or number) in the sample $E_{CALIB}$ also being known.

A second type of calibration, referred to as internal calibration, can be carried out by incorporating in the sample E to be analyzed at least one other sample E* of known marking (equivalent to the components of interest but with a different known mass, their concentration or number in the same E* also being known) components (in the example chosen, these are proteins).

The processing chain 12 can be calibrated by internal or external calibration, one not excluding the other. In particular, the product of the aforementioned three gains Ge, Gf and Gc can be determined by internal calibration.

A direct analytical modeling of the signal Y will now be proposed, in which at least one parameter related to the molecular mass of the components of the sample E and technical parameters of the processing chain participate. This modeling is constructed around specificities of the MEMS or NEMS sensor of the mass spectrometer 22. Thus only the molecules actually adsorbed on this sensor are taken into account in the model. The actual composition of the sample E supplied as an input to the processing chain 12 can however easily be found from the number and mass of the molecules adsorbed as well as known gain parameters.

In order to be able to apply suitable statistical processing methods to the signal Y, the adsorptions of molecules on the MEMS or NEMS sensor of the mass spectrometer 22 are counted in observation windows of T regular samples and the parameters are expressed by discretized vectors with T components. Thus, for example, the observed signal Y becomes a discretized vector $\underline{Y}$ with T components.

In these same observations windows, the time distribution of the adsorbed masses is denoted m. In continuous time and according to the model chosen, this time distribution is a weighted Dirac comb expressed in the form $$m(t) = \sum_{i=1}^{I} M_i \cdot \delta(t - t_i),$$

where I is the number of molecules (or molecular assemblies) detected as adsorbed in an observation window, each molecule (or molecular assembly) adsorption detection being termed an event, $M_i$ the respective masses of the I molecules adsorbed, $\delta$ the Dirac distribution and $t_i$ the respective instants of adsorption of the molecules (or molecular assemblies). In discrete time, this distribution becomes a vector $\underline{m}$ with T components, including I non-zero components. This time distribution can also be expressed in a variant in the form of a list m comprising, for each event, the detected mass ($M_i$) and the detection instant ($t_i$). In other words, when m represents a list, m={($M_i$, $t_i$)}.

In addition, the time distribution of the adsorption sites is denoted z. In continuous time and according to the model chosen, this time distribution is a piecewise continuous Dirac signal expressed in the form:

z(t)=0 if $t<t_1$, z(t)=$z_i$ if $t \in [t_{i+1}\ ;\ _{ii+1}[$, z(t)=$z_I$ if $t>t_I$, where the $z_i$, $1 \leq i \leq I$ are the respective adsorption sites. In discrete time, this distribution becomes a vector $\underline{z}$ with T components. This parameter $\underline{z}$ may be termed an "uncertain" parameter in that it is liable to vary randomly from one biological processing to another. However, given that at each instant it is possible to know the position of the last molecule adsorbed by means of the position detection device 24, there is no need to model it by a prior probability law.

The drop in frequency caused by the MEMS or NEMS sensor at each adsorption is dependent on the electromechanical characteristics of this sensor according to a deterministic function denoted c of each pair ($M_i$, $z_i$). An example of such a function can be deduced from the aforementioned article by Dohn et al. The values that this function takes at each detection instant $t_i$ can be denoted c($M_i$, $z_i$). Ideally, the MEMS or NEMS sensor of the mass spectrometer 22 is chosen so as to be sufficiently sensitive to detect an appreciable drop in voltage at each adsorption and sufficiently rapid to temporally discriminate the successive drops in frequency due to the successive adsorptions. Thus each drop in frequency observable can be considered to be immediate and perfect.

Hereinafter, the following will be noted:

$$c(\underline{m}, \underline{z}) = \sum_{i=1}^{I} c(M_i, z_i) \cdot \delta(t - t_i),$$

The change in the natural resonant frequency of the MEMS or NEMS sensor of the mass spectrometer 22 in an observation window can then be expressed in the following form:

$$f(t) = f_0 - \int_0^t \left( \sum_{i=1}^{I} c(M_i, z_i) \cdot \delta(u - t_i) \right) du.$$

In discrete time, this resonant frequency becomes a vector $\underline{f}$ the components of which are written in the form:

$$\underline{f}(t) = f_0 - \sum_{u=1}^{t} \sum_{i=1}^{I} c(M_i, z_i) \cdot \delta(u - t_i).$$

Consequently the theoretical signal g supplied at the output of the electronic reading system 26 can be written as the convolution product of the aforementioned resonant frequency $\underline{f}$ and the filter $\underline{h}$ which represents the reading loop of this system 26. In discrete time, the equation is written $\underline{g}=\underline{f}*\underline{h}$.

It suffices to know $f_0$ (or the equivalent $g_0$) as well as the functions c and $\underline{h}$ for the outputs $\underline{f}$ and g to be completely determined.

Finally, in order to take account of the model imperfections as well as the interferences, it is considered that the observed signal $\underline{Y}$ is related to g by the addition of a noise of parameter $\epsilon$, this parameter being for example the variance of the noise. This parameter $\epsilon$ can be termed an "uncertain" parameter in that it is liable to vary randomly from one biological processing to another. It can therefore advantageously be modeled according to a predetermined prior probability law, for example an inverse-gamma law IGAM($\epsilon | k_\epsilon$, $T_\epsilon$) of form $k_\epsilon$, and intensity $T_\epsilon$, the last two parameters representing the prior knowledge on the noise denoted $\theta_\epsilon$.

The observed signal $\underline{Y}$ is supplied as an input to the processing device 14. More precisely, the processing device 14 comprises a processor 28 connected to storage means comprising in particular at least one programmed sequence of instructions 30 and a modeling database 32.

The database 32 comprises the parameters of a direct analytical modeling of the signal $\underline{Y}$ according to:
- the molecular mass parameter $\underline{m}$ that makes it possible to find a knowledge of the mass spectrum Sp of the components of the sample E,
- the time distribution parameter z of the adsorption sites on the MEMS or NEMS sensor,
- the aforementioned technical parameters Ge, Gf, Gc, $f_0$, $g_0$, $\epsilon$ of the biological processing chain 12,
- the functions c, $\underline{f}$, $\underline{h}$ and g, also characteristics of the biological processing chain 12, and
- other theoretical parameters for refining the explanation of the parameter $\underline{m}$ in various embodiments that will be detailed below.

On supply of the signal actually observed $\underline{Y}$, the programmed sequence of instructions 30 is designed to solve the inversion of this analytical model in a Bayesian context by a posterior estimation based on probability models, for example prior models, of at least some of the aforementioned parameters.

The sequence of instructions 30 and the database 32 are functionally presented as distinct in FIG. 1, but in practice they may be distributed differently in data files, source codes or computer libraries without this in any way changing the functions fulfilled.

In a first embodiment, in which it is assumed that the molecules of the sample have a continuous distribution of masses, the parameter $\underline{m}$ can be refined by introducing a theoretical parameter g with binary values representing each adsorption on the MEMS or NEMS sensor. This parameter is a vector the components of which take the form:

$$q(t) = \sum_{i=1}^{I} \delta(t - t_i).$$

It will be recalled that the variable $t_i$ designates the respective instants of adsorptions, an adsorption corresponding to the detection of a molecule or a molecular assembly on the MEMS or NEMS sensor. Thus the variable g takes into account the discrete character of the detection of the molecules or molecular assemblies by a sensor, which constitutes a particularity of MEMS or NEMS sensors.

In an equivalent manner to what was stated for $\underline{m}$, the knowledge of these adsorption instants $t_i$ and of the mass detected at each of these instants makes it possible to form a list of events, each event corresponding to the detection of a molecule or a molecular assembly. Typically, a pair $(M_i, t_i)$, representing the mass $M_i$ detected at instant $t_i$, is attributed to each event of index i. The list is formed by the set of these pairs, each pair being associated with a detection. The formalism of such a list takes into account the discrete character of the detection of the molecules or molecular assemblies by a sensor, a specific character of MEMS or NEMS sensors, as previously indicated.

The parameter $\underline{m}$ takes a non-zero value only when $\underline{q}$ is non-zero. Consequently $\underline{m}$ can be expressed in the form $\underline{m} = \underline{\mu} \cdot \underline{q}$ where $\underline{\mu}$ represents the estimation of the continuous mass of the molecules at each instant. The values of $\underline{\mu}$ have a sense only where the values of $\underline{q}$ are not zero.

In the model chosen, the parameter $\underline{q}$ is "uncertain" and itself subject to another theoretical "uncertain" parameter P indicating the probability that the components of $\underline{q}$ take the value 1 in an observation window. In other words, the parameter P is a scalar that models the time density of the adsorptions. It can advantageously be modeled according to a predetermined prior probability law, for example a beta law $BET(P|a_P, b_P)$ of parameters of form $a_P$ and $b_P$, these last two parameters representing the prior knowledge on P denoted $\theta_P$. As for the vector $\underline{q}$, it can be modeled by a Bernoulli law, the probability that $\underline{q}$ is equal to 1 at each instant being given by the parameter P.

In the model chosen also, the vectorial parameter $\underline{\mu}$ is "uncertain" and its T independent components $\mu_k$ are modeled according to a predetermined prior probability law, for example a gamma law $GAM(\mu_k|k_m, T_m)$ of form $k_m$ and intensity $T_m$, these last two parameters representing the prior knowledge on the molecular mass parameter denoted $\theta_m$.

In summary, some of the aforementioned parameters or functions are "uncertain" or dependent on "uncertain" parameters and are possibly, for some of them, modeled a priori by probability laws: it is the case of technical or theoretical parameters/functions $\epsilon$, $\underline{g}$, $\underline{f}$, $\underline{z}$, $\underline{q}$ and P of the biological processing chain 12 and of molecular mass parameters $\underline{m}$ and $\underline{\mu}$. These parameters, among which are the vectors $\underline{m}$ and $\underline{\mu}$, are estimated by inversion of the direct model according to a method that will be detailed with reference to FIG. 3.

Figure 2:
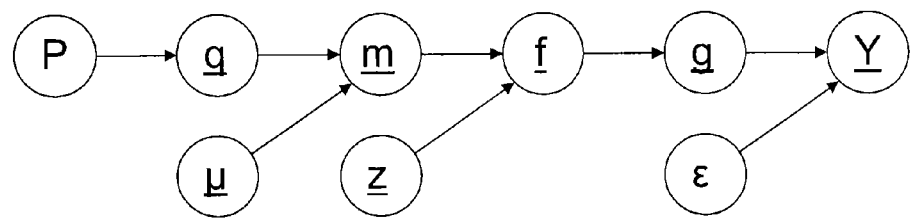
FIG. 2 illustrates a first analytical modeling of a processing chain of the device of FIG. 1, according to a first embodiment of the invention.

As illustrated in FIG. 2 in the context of the first embodiment, these uncertain parameters are defined as having a probabilistic dependency relationship with each other, leading to a hierarchical global probabilistic model.

Thus, in the particular example of the first embodiment, the vector $\underline{q}$ representing the adsorptions is defined as dependent on the adsorption density parameter P. This is because the random variable $\underline{q}$ follows a Bernoulli probability law that varies according to the value of the random variable P.

Likewise, the vector $\underline{m}$ representing the molecular mass of the components of the sample E is dependent on the vector $\underline{q}$ and the parameter $\underline{\mu}$, as defined previously, by the equation $\underline{m} = \underline{\mu} \cdot \underline{q}$.

Likewise, the function $\underline{f}$ representing the temporal change in the natural resonant frequency of the MEMS or NEMS sensor, defined by its parameter $f_0$ and the function $c(\underline{m}, \underline{z})$, is dependent on the vectors $\underline{m}$ and $\underline{z}$, which corresponds to a realistic model of the sensor.

Likewise, the function $\underline{g}$ representing the output of the reading system 26, defined by its parameter $g_0$ and the filtering function $\underline{h}$ implementing the reading loop, is dependent on the function $\underline{f}$ as defined previously by the equation $\underline{g} = \underline{f} * \underline{h}$.

Finally, the observed signal $\underline{Y}$ depends directly on the function $\underline{g}$ and the noise parameter $\epsilon$.

Consequently, as can be seen in FIG. 2, at a first hierarchy level of the probabilistic model, the observed signal $\underline{Y}$ depends solely on random variables $\underline{g}$ and $\epsilon$, the latter being defined by the nature of its prior probabilistic model and the prior knowledge $\theta_\epsilon$. At a second hierarchy level of the probabilistic model the random variable $\underline{g}$ depends solely on the random variable $\underline{f}$. At a third hierarchy level of the probabilistic model, the random variable $\underline{f}$ depends only on the random variables $\underline{m}$ and $\underline{z}$, the latter being in fact known by virtue of the presence of the detection device 24. At a fourth hierarchy level of the probabilistic model, the random variable $\underline{m}$ depends only on the random variables $\underline{q}$ and $\underline{\mu}$, the latter being defined by the nature of its prior probabilistic model and the prior knowledge $\theta_m$. Finally, at a fifth hierarchy level of the probabilistic model, the random variable $\underline{q}$ depends only on the random variable P, the latter being defined by the nature of its prior probabilistic model and the prior knowledge $\theta_P$. It will be noted in particular that this hierarchical model, through the dependency defined between $\underline{f}$ on the one hand and $\underline{m}$, $\underline{z}$, on the other hand, gives rise to a hierarchy between the biological mass parameters of the sample E and the technical parameters of the processing chain 12: it thus has in fact a first technical stage (second and third levels) dependent on a second biological stage (fourth and fifth levels), each of these two stages itself being able to have an internal hierarchy according to the model adopted.

On the basis of this hierarchical probabilistic model, a molecular mass parameter estimation method used by the processor 28 by execution of the sequence of instructions 30 will now be described. According to a first main phase, this method effects an inversion of the probabilistic model constructed in the light of the signal observed $\underline{Y}$. This inversion makes it possible to estimate the mass parameter $\underline{m}$ of the molecules adsorbed on the MEMS or NEMS sensor. According to a second main spectrum reconstruction phase, this method makes it possible to estimate the mass spectrum Sp of the components of the sample E from the parameter $\underline{m}$.

According to the first inversion phase of this method, the parameter $\underline{m}$ is estimated conjointly with the estimation of all the random variables $\epsilon$, $\underline{g}$, $\underline{f}$, $\underline{z}$, $\underline{m}$, $\underline{\mu}$, $\underline{q}$ and P by applying an estimator to the joint posterior probability law of these random variables in the light of the observation $\underline{Y}$ or, in an equivalent fashion, on the joint probability law of these random variables and the observation $\underline{Y}$. This is because these two probability laws are linked by the Bayes rule to the probability of the observation $\underline{Y}$ (or marginal law) by the following equation:

$$p(\underline{Y}, \epsilon, \underline{g}, \underline{f}, \underline{z}, \underline{m}, \underline{\mu}, \underline{q}, P) = p(\epsilon, \underline{g}, \underline{f}, \underline{z} \underline{m} \underline{\mu} \underline{q}, P | \underline{Y}) \cdot p(\underline{Y}).$$

The joint posterior probability law is also developed in the following way, still according to the Bayes rule:

$$p(\varepsilon, \underline{g}, \underline{f}, \underline{z}, \underline{m}, \underline{\mu}, \underline{q}, P \mid \underline{Y}) =$$

$$\frac{p(\underline{Y} \mid \varepsilon, \underline{g}, \underline{f}, \underline{z}, \underline{m}, \underline{\mu}, \underline{q}, P) \cdot p(\varepsilon, \underline{g}, \underline{f}, \underline{z}, \underline{m}, \underline{\mu}, \underline{q}, P)}{p(\underline{Y})}.$$

Although the law of likelihood $p(\underline{Y} \mid \varepsilon, \underline{g}, \underline{f}, \underline{z}, \underline{m}, \underline{\mu}, \underline{q}, P)$ can be expressed analytically and although the joint law of the parameters $p(\varepsilon, \underline{g}, \underline{f}, \underline{z}, \underline{m}, \underline{\mu}, \underline{q}, P)$ can be developed into a product of conditional prior probability laws that can be modeled by experiment or by a specific calibration, the marginal law $p(\underline{Y})$ is not known and not calculatable analytically. Consequently the joint posterior probability law can also not be calculated analytically since this multiplying factor $p(\underline{Y})$, which however remains constant for all the parameters, is not known. This unknown multiplying factor is therefore not detrimental.

The result however is that the calculation of an estimator, such as the expectation a posteriori, median a posteriori or maximum a posteriori estimator, on this joint posterior law cannot be done analytically in a simple fashion.

For its part, the joint probability law of the random variables and the observation develops in the following manner, by means of the hierarchical model of FIG. 2:

$$p(\underline{Y}, \varepsilon, \underline{g}, \underline{f}, \underline{z}, \underline{m}, \underline{\mu}, \underline{q}, P) =$$

$$\begin{cases} p(\underline{Y} \mid \varepsilon, \underline{g}) \cdot p(\varepsilon \mid \theta_\varepsilon) \cdot p(\underline{g} \mid \underline{f}) \cdot p(\underline{f} \mid \underline{z}, \underline{m}) \cdot p(\underline{z} \mid \theta_z) \cdot p(\underline{m} \mid \underline{\mu}, \underline{q}) \cdot \\ p(\underline{\mu} \mid \theta_m) \cdot p(\underline{q} \mid P) \cdot p(P \mid \theta_P) \end{cases}$$

In the light of the deterministic dependencies between some of these parameters and the prior probability laws chosen for others (as indicated previously for the parameters $\varepsilon$, $\underline{\mu}$, $\underline{q}$ and P), this knowledge being able in particular to be acquired by an external calibration, the joint law of random variables and observation is easily marginalized into:

$$p(\underline{Y}, \varepsilon, \underline{\mu}, \underline{q}, P) =$$

$$\begin{cases} N(\underline{Y} \mid c(\underline{\mu} \cdot \underline{q}, \underline{z}) * \underline{h}, \varepsilon \cdot I_T) \cdot \prod_{i=1}^{T} GAM(\mu_i \mid k_m, T_m) \cdot (P^{\Omega(\underline{q},1)} \cdot (1-P)^{\Omega(\underline{q},0)}) \cdot \\ IGAM(\varepsilon \mid k_\varepsilon, T_\varepsilon) \cdot BET(P \mid a_P, b_P), \end{cases}$$

where $\Omega(x,i)$ is a function returning the number of components of the vector x equal to i.

However, the calculation of an estimator, such as the expectation a posteriori, median a posteriori or maximum a posteriori estimator, on this joint law also marginalized, cannot be done analytically in a simple manner.

To get round the impossibility of directly calculating such an estimator on the aforementioned joint posterior law or marginalized joint law, it is equivalent and advantageous to proceed with a numerical stochastic sampling of each of the unknown parameters of the marginalized joint law, that is to say each of the parameters $\varepsilon$, $\underline{\mu}$, $\underline{q}$ and P, according to the conditional posterior probability law that it satisfies, in accordance for example with the known Markov Chain Monte-Carlo method (the MCMC sampling method), a method that constitutes an approximation of a random drawing under the joint law. The MCMC numerical sampling can in particular be carried out by iterative methods of the Gibbs stochastic sampling type optionally involving the Metropolis-Hastings algorithm (or equivalent) and the estimator, for example expectation a posteriori, can then be approximated simply by the mean values of the respective samplings.

It is shown indeed that whereas the joint probability law cannot be expressed analytically by means of prior probabilities (conditional or not), it is on the other hand the case with the aforementioned conditional posterior laws, as will now be detailed.

In particular, because of the hierarchy of the probabilistic model of FIG. 2, having regard also to the marginalized joint law detailed previously and its parameters independent from $\underline{\mu}$, it is easily shown that the conditional posterior probability law followed by the parameter $\underline{\mu}$ takes the following form:

$$p(\underline{\mu} \mid \underline{Y}, \varepsilon, \underline{q}, P) = N(\underline{Y} \mid c(\underline{\mu} \cdot \underline{q}, \underline{z}) * \underline{h}, \varepsilon \cdot I_T) \cdot \prod_{i=1}^{T} GAM(\mu_i \mid k_m, T_m).$$

It is shown in the same way that:

$$p(\underline{q} \mid \underline{Y}, \varepsilon, \underline{\mu}, P) = N(\underline{Y} \mid c(\underline{\mu} \cdot \underline{q}, \underline{z}) * \underline{h}, \varepsilon \cdot I_T) \cdot (P^{\Omega(\underline{q},1)} \cdot (1-P)^{\Omega(\underline{q},0)}),$$

$$p(\varepsilon \mid \underline{Y}, \underline{\mu}, \underline{q}, P) = N(\underline{Y} \mid c(\underline{\mu} \cdot \underline{q}, \underline{z}) * \underline{h}, \varepsilon \cdot I_T) \cdot IGAM(\varepsilon \mid k_\varepsilon, T_\varepsilon)$$

$$= IGAM\left(\varepsilon \mid \left(k_\varepsilon + \frac{T}{2}\right), (T_\varepsilon + 0,5 \cdot \|\underline{Y} - c(\underline{\mu} \cdot \underline{q}, \underline{z}) * \underline{h}\|^2)\right),$$

and $$p(P \mid \underline{Y}, \varepsilon, \underline{\mu}, \underline{q}) = (P^{\Omega(\underline{q},1)} \cdot (1-P)^{\Omega(\underline{q},0)}) \cdot BET(P \mid a_P, b_P)$$

$$= BET(P \mid (a_P + \Omega(\underline{q}, 1)), (b_P + \Omega(\underline{q}, 0))).$$

The above equations show that the conditional posterior probability laws of the unknown parameters $\varepsilon$, $\underline{\mu}$, $\underline{q}$ and P can be expressed analytically since they are proportional to prior distributions or probabilities products that can either be modeled or defined by learning.

More precisely, the posterior probability for the noise parameter $\varepsilon$ follows a gamma-inverse law so that the sampling of this parameter can be done simply and conventionally in the context of an iterative Gibbs sampling method.

Likewise, the posterior probability for the parameter P follows a beta law so that the sampling of this parameter can be done simply and conventionally in the context of an iterative Gibbs sampling method.

On the other hand, the posterior probability for the parameter $\underline{q}$ is expressed in the form of a product of a normal law and gamma laws. This posterior probability does not have a simple expression, so that the sampling of the parameter $\underline{q}$ cannot be done simply in the context of an iterative Gibbs sampling method. It will be necessary to use a random walk sampling technique, such as the Metropolis-Hastings with Random Walk (MHRW) algorithm or a similar algorithm. Such a sampling technique requires defining at each iteration a neighborhood of the parameter concerned as estimated at the previous iteration in order to proceed with the drawing of new value. The parameter $\underline{\mu}$ being by hypothesis a vector with continuous values, this concept of neighborhood will be conventional. More precisely, the posterior law is estimated numerically in a neighborhood of the value of the previous sample; this law is normalized, and then a new sample is drawn according to the posterior law; if this sample does not increase the joint probability, it is accepted with a probability dependent on the ratio of the joint probability with the old sample and with the new sample.

Likewise, the posterior probability for the parameter $q$ is expressed in the form of the product of a normal law and a Bernoulli law. This posterior probability also does not have a simple expression, so that the sampling of the parameter $q$ cannot be done simply in the context of an iterative Gibbs sampling method. It will be necessary to use a random walk sampling technique, such as the Metropolis-Hastings with Random Walk (MHRW) algorithm or an approximate algorithm, making it necessary to define a neighborhood of the parameter concerned. The parameter being by hypothesis a vector with binary values, a particular concept of neighborhood will now be defined.

Whereas in the prior art some conventional algorithms consider that the neighborhood of a vector is all the vectors differentiated therefrom only by one component, the neighborhood of the binary-component vector such as g is advantageously defined as consisting of binary vectors:
- such that an adsorption has been removed (i.e. a component with 1 less),
- such that an adsorption has been added (i.e. a component with 1 more),
- such that an adsorption is shifted by few samples (i.e. a component with 1 shifted), and
- such that two adsorptions have been grouped together (i.e. two neighboring components with 1 grouped together in a single one).

This new definition of neighborhood has an important impact on the good convergence of the sampling. In particular, it makes it possible to greatly limit the risk of converging towards a local optimum.

Figure 3:
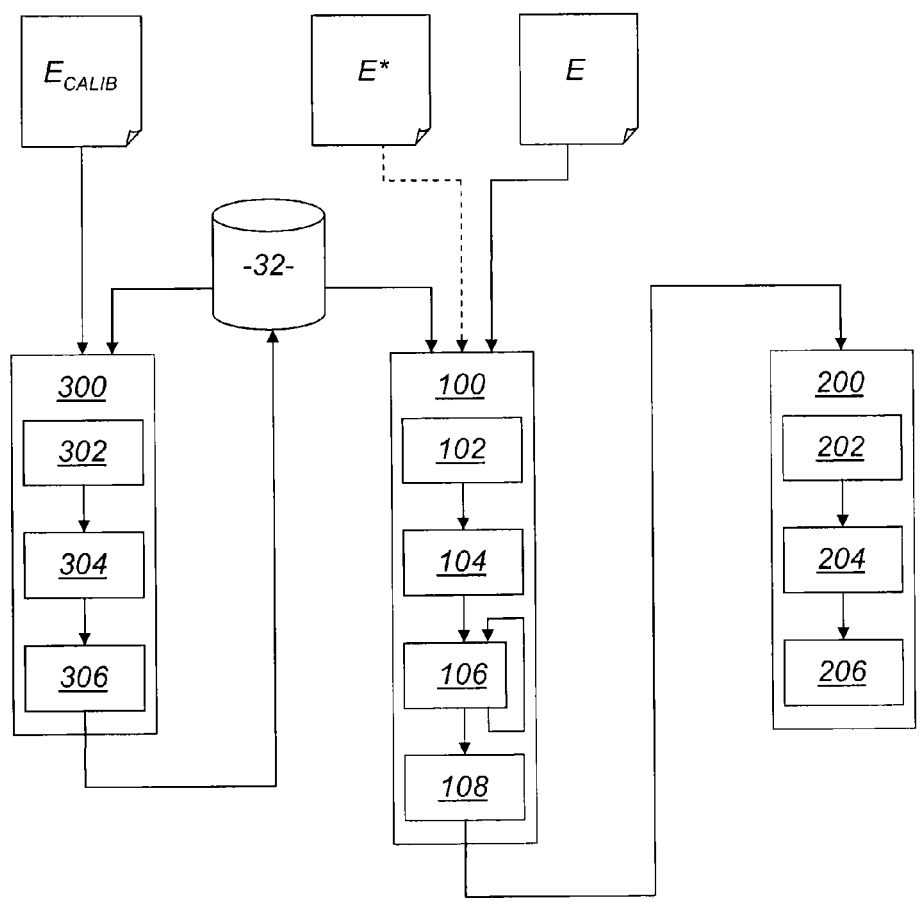
FIG. 3 illustrates the successive steps of a method for estimating a molecular mass parameter used by a signal processing device of the device of FIG. 1.

In the light of the above and with reference to FIG. 3, a method for estimating a molecular mass parameter used by the processor 28 by executing the sequence of instructions 30 comprises a first main phase 100 of conjoint estimation of the so-called "uncertain" parameters of a biological sample E the composition of which is not known, including in particular at least the parameters $\mu$ and $q$, by inversion of the model. It then comprises a second main phase 200 of mass spectrum reconstruction from the knowledge of $\underline{m}=\mu \cdot q$.

The execution of the first main conjoint estimation phase 100 and the second main reconstruction phase 200 assumes that a certain number of data and parameters are already known and recorded in the database 32, namely:
- the so-called "certain" or constant parameters of the biological processing chain 12, that is to say those that are invariant from one biological processing to another, and
- the parameters of the prior probability models, conditional or not, of "uncertain" parameters from which the conditional posterior probability models of each of the other parameters can be determined.

When at least some of these data are not known, the molecular mass parameter estimation method can optionally be supplemented by an external calibration phase 300 preceding the two main conjoint estimation 100 and reconstruction 200 phases: for determining the "certain" parameters not yet known and their recording in the database 32, and/or
- for determining stable parameters (for example mean or variance) of the prior probability models of the "uncertain" parameters and their recording in the database 32.

The main conjoint estimation phase 100 comprises a first measurement step 102 during which, in accordance with the diagram in FIG. 1, the sample E passes right through the processing chain 12 of the device 10 to supply an observed signal $\underline{Y}$.

Next, during an initialization step 104, the random variables $\epsilon$, $\mu$, $q$ and $P$ are each initialized by the processor 28 to a first value $\epsilon^{(0)}$, $\mu^{(0)}$, $q^{(0)}$ and $P^{(0)}$. This step can be carried out in several ways:
- initialization to zero values,
- initialization by sampling the variables with their prior probability laws, running through the probabilistic model of FIG. 2 from the highest level (on the left) to the lowest level (on the right), or
- initialization with an inexpensive but less effective method, such as for example deriving the signal $\underline{Y}$ in order to initialize $q$, and keeping the N lowest values of the derivative, etc.

The initialization 104 is also the step enabling the pre-allocation of memory necessary for the correct implementation of the method.

The processor 28 then executes, by applying a Markov chain Monte-Carlo algorithm and, on an index k varying from 1 to kmax, a Gibbs sampling loop 106 for each of the random variables initialized with a view to their respective conditional posterior probability laws as expressed analytically. kmax is the maximum value taken by the index k before a predetermined stop criterion is satisfied. The stop criterion is for example a maximum number of iterations fixed a priori, the satisfaction of a stability criterion (such as the fact that an additional iteration has no significant impact on the chosen estimator of the random variables) or other.

More precisely, for k varying from 1 to kmax, the loop 106 comprises the following successive samplings:
- generating a sample $\epsilon^{(k)}$ from the posterior law $p(\epsilon|\underline{Y}, \mu^{(k-1)}, q^{(k-1)}, P^{(k-1)})$,
- defining the neighborhood of the parameter $\mu$ from the value $\mu^{(k-1)}$,
- generating a sample $\mu^{(k)}$, in a neighborhood of $\mu^{(k-1)}$ from the posterior law $p(\mu|\underline{Y}, \epsilon^{(k)}, q^{(k-1)}, P^{(k-1)})$,
- defining the neighborhood of the parameter $q^{(k)}$, from the value $q^{(k-1)}$,
- generating a sample $q^{(k)}$, in the neighborhood of $q^{(k-1)}$ from the posterior law $p(q|\underline{Y}, \epsilon^{(k)}, \mu^{(k)}, P^{(k-1)})$, and
- generating a sample $P^{(k)}$ from the posterior law $p(P|\underline{Y}, \epsilon^{(k)}, \mu^{(k)}, q^{(k)})$.

In addition, at each iteration, the marginalized joint law is estimated and its value is stored in memory with the current values $\epsilon^{(k)}$, $\mu^{(k)}$, $q^{(k)}$, $P^{(k)}$.

The processor 28 next executes an estimation step 108 during which an estimation is retained for each sampled unknown parameter. Each parameter is estimated from all the sample values that it has taken and which have been taken by the marginalized joint law as the iterations progress.

All the values taken into account then can be reduced to the results of iterations lying between an index kmin and the index kmax, kmin being a predetermined "heating time" value judged necessary so that, during the Gibbs sampling, the random drawing law converges towards the joint posterior law, the latter also being able to be called the target law. For example, for a loop of kmax=500 samples, a heating time value of kmin=200 (that is to say 40% of the total number of iterations) appears reasonable.

It is thus possible, as required, in the case of an unknown parameter with discrete values (for example the parameter g):
- to keep the value of the sample that led to the highest value of the marginalized joint law,
- to average and then discretize the values of N (to be defined) samples that brought the N highest values of the marginalized joint law, to average and then discretize the value of the last N (to be defined, for example kmax-kmin) samples (expectation a posteriori estimator), to retain the sample value that appears most often between the indices kmin and kmax (maximum a posteriori estimator), etc.

In the case of an unknown parameter with continuous values (for example the parameter $\underline{\mu}$), it is possible:

to keep the value of the sample that led to the highest value of the marginalized joint law, to average the values of N (to be defined) samples that brought the N highest values of the marginalized joint law, to average the values of the last N (to be defined, for example kmax-kmin) samples (expectation a posteriori estimator), to average the values of the N (to be defined) samples that brought the N highest values of the joint law and such that the unknown parameters with discrete values are equal to their estimated value (for example, averaging only the values of samples of $\underline{\mu}$ relating to iterations for which the sample of $\underline{q}$ takes the value of its estimate), averaging the values of the last N (to be defined) samples such that the unknown parameters with discrete values are equal to their estimated value, etc.

The estimation step 108 thus supplies estimated values $\hat{\epsilon}$, $\hat{\underline{\mu}}$, $\hat{\underline{q}}$ and $\hat{P}$ for each of the unknown parameters $\epsilon$, $\underline{\mu}$, $\underline{q}$ and P. An estimated value $\hat{\underline{m}} = \hat{\underline{\mu}} \cdot \hat{\underline{q}}$ is directly derived for the parameter m that contains the quantity and mass information on the molecules adsorbed by the MEMS or NEMS. This last step of the first main conjoint estimation phase 100 is followed by the second main reconstruction phase 200.

During a first step 202 of the second main reconstruction phase 200, the adsorptions detected but for which the location on the MEMS or NEMS sensor leads to a drop in frequency of value $$\frac{c(M_i, z_i)}{\underset{z_i}{\mathrm{Max}}(c(M_i, z_i))}$$

below a predetermined threshold (for example 0.25) are eliminated. These eliminations are termed "rejects in z". The level of rejects in z $TR_z$ is also calculated at this step. During a following step 204, a histogram of the parameter $\underline{m}$ is calculated, the latter corresponding to the mass spectrum of the sample E. This calculation step is conventional and will not be detailed.

Finally, during a step 206, this histogram is multiplied by a constant that proves to be the inverse of a gain, in particular the inverse of the global gain of the processing chain 12, namely the product Ge.Gf.Gc, multiplied by the inverse of $(1-TR_z)$ (the 1's complement of the level of rejects in z calculated at step 202). In this way the mass spectrum Sp of the components of the sample E is obtained, which is, like the parameter $\underline{m}$, a molecular mass parameter characteristic of the molecular profile of this sample.

In a variant of the first embodiment that has just been described, an internal calibration can be carried out by incorporating in the sample E, at step 102, a sample E* of known marking weighted components.

A first consequence of such an internal calibration carried out during the measurement step 102 is to add a prior knowledge to at least some of the parameters of the processing chain 12. In particular, the components $\mu_k$ of the vectorial parameter $\underline{\mu}$ being modeled on a gamma law $GAM(\mu_k|k_m, T_m)$, the prior knowledge $\theta_m$ on this parameter can be more concentrated around the weighted masses introduced.

Another consequence concerns step 206, the inverse of the gain used for weighting the histogram of the parameter $\underline{m}$ not being known a priori but estimated by the processing device 14 by means of the internal calibration.

The phase of external calibration 300 of the biological processing chain 12 comprises a first measurement step 302 during which, in accordance with the diagram in FIG. 1, the external calibration protein sample $E_{CALIB}$ passes right through the processing chain 12 of the device 10 to supply an observed signal $\underline{Y}_{CALIB}$.

The processing applied by the processor 28 to the signal $\underline{Y}_{CALIB}$ consists of determining the values not yet known of "certain" parameters, that is to say parameters that in reality remain relatively constant from one biological processing to another. These "certain" parameters are then considered and modeled by constants in the biological processing chain 12. It is the case for example of the various gains of the processing chain 12 such as Ge, Gf and Gc, the aforementioned parameters $f_0$ or $g_0$, the filtering function $\underline{h}$ of the reading loop, etc. This processing can also consist of determining stable parameters (for example mean or variance) of the prior probability models of "uncertain" parameters such as those aforementioned. These stable parameters are then also considered and modeled by constants.

In the external calibration protein sample, some of the "uncertain" parameters are this time known, such as the molecular mass parameter $\underline{m}$ or the mass spectrum Sp, but, as for the first main phase 100, the determination is made by applying a numerical sampling in accordance with the Markov chain Monte-Carlo method. It is done this time however in a conventional fashion on the unknown "certain" parameters and is illustrated by the reference 304. The step 304 therefore reproduces some of the determination steps 104, 106 and 108 of the main phase 100.

Finally, during a last step 306 of the first external calibration phase, the "certain" and stable parameters determined at the previous step are recorded in the database 32.

If during this external calibration several molecules of known concentrations are introduced, it is necessary to calculate the "certain" and stable parameters (including the gain constants) for each of the types of molecule. Next, it suffices for example to retain the mean of these calculations, their median, or the mean of the less extreme values. This method can also be applied in internal calibration, where applicable.

In a second embodiment, in which it is assumed that the molecules of the sample all have same single mass $M_0$, the parameter $\underline{m}$ can be refined by introducing the theoretical parameter $\underline{q}$ mentioned in the first embodiment. It can then be expressed in the form $\underline{m} = M_0 \cdot \underline{q}$ where $M_0$ is a constant.

Figure 4:
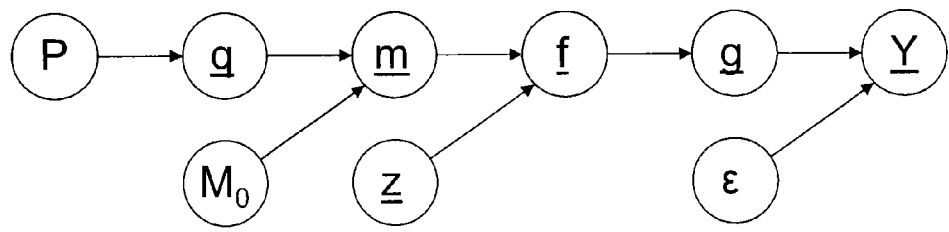
FIG. 4 illustrates a second analytical modeling of a processing chain of the device of FIG. 1, according to a second embodiment of the invention.

In this new model chosen, the parameter $M_0$ is uncertain and is modeled according to a predetermined prior probability law, for example a gamma law $GAM(M_0|k_m, T_m)$ of form $k_m$ and intensity $T_m$, these last two parameters representing the prior knowledge on the molecular mass parameter denoted $\theta_m$. As illustrated in FIG. 4 in the context of the second embodiment, the "uncertain" parameters of the new model, all identical to those of the previous model with the exception of $M_0$, are defined as having a probabilistic dependency relationship between them, leading to a hierarchical global probabilistic model.

Thus the parameter $\underline{q}$ is dependent on the parameter P, the parameter $\underline{m}$ dependent on the parameter $\underline{q}$ and on the parameter $M_0$, as defined previously by the equation $\underline{m} = M_0 \cdot \underline{q}$, the function $\underline{f}$ dependent on the parameters $\underline{m}$ and $\underline{z}$, the function $\underline{g}$ dependent on the function $\underline{f}$ and the observed signal $\underline{Y}$ dependent on the function $\underline{g}$ and the noise parameter $\epsilon$.

Consequently, as can be seen in FIG. 4, at a first hierarchy level of the probabilistic model, the observed signal $\underline{Y}$ depends only on the random variables $\underline{g}$ and $\epsilon$, the latter being defined by the nature of its prior probabilistic model and the prior knowledge $\theta_\epsilon$. At a second hierarchy level of the probabilistic model, the random variable $\underline{g}$ depends only the random variable $\underline{f}$. At a third hierarchy level of the probabilistic model, the random variable $\underline{f}$ depends only on the random variables $\underline{m}$ and $\underline{z}$, the latter in fact being known because of the presence of the detection device 24. At a fourth hierarchy level of the probabilistic model, the random variable $\underline{m}$ depends only on the random variables $\underline{q}$ and $M_0$, the latter being defined by the nature of its priori probabilistic model and the prior knowledge $\theta_m$. Finally, at a fifth hierarchy level of the probabilistic model, the random variable $\underline{q}$ depends only on the random variable P, the latter being defined by the nature of its prior probabilistic model and the prior knowledge $\theta_P$.

On the basis of this hierarchical probabilistic model, the molecular mass parameter estimation method described previously applies in the same way for an estimation of the parameter $\underline{m}$ and the mass spectrum Sp.

According to the first inversion phase of this method, the parameter $\underline{m}$ is estimated conjointly with the estimation of all the random variables $\epsilon$, $\underline{g}$, $\underline{f}$, $\underline{z}$, $\underline{m}$, $M_0$, $\underline{q}$ and P by applying an estimator to the joint posterior probability law of these random variables in the light of the observation $\underline{Y}$ or, in an equivalent fashion, on the joint probability law of these random variables and the observation $\underline{Y}$.

In particular, the joint probability law of the random variables and the observation is developed in the following way, by means of the hierarchical model of FIG. 4:

$$p(\underline{Y}, \epsilon, \underline{g}, \underline{f}, z, \underline{m}, M_0, \underline{q}, P) =$$
$$\begin{cases} p(\underline{Y} | \epsilon, \underline{g}) \cdot p(\epsilon | \theta_\epsilon) \cdot p(\underline{g} | \underline{f}) \cdot p(\underline{f} | z, \underline{m}) \cdot p(z | \theta_z) \cdot \\ p(\underline{m} | M_0, \underline{q}) \cdot p(M_0 | \theta_m) \cdot p(\underline{q} | P) \cdot p(P | \theta_P). \end{cases}$$

In the light of the deterministic dependencies between some of these parameters and the prior probability laws chosen for others (as indicated previously for the parameters $\epsilon$, $M_0$, $\underline{q}$ and P), this knowledge being able in particular to be acquired by an external calibration, the joint law of the random variables and the observation is easily marginalized as:

$$p(\underline{Y}, \epsilon, M_0, \underline{q}, P) =$$
$$\begin{cases} N(\underline{Y} | c(M_0 \cdot \underline{q}, z) * \underline{h}, \epsilon \cdot I_T) \cdot GAM(M_0 | k_m, T_m) \cdot \left(P^{\Omega(\underline{q}, 1)} \cdot (1-P)^{\Omega(\underline{q}, 0)}\right) \cdot \\ IGAM(\epsilon | k_\epsilon, T_\epsilon) \cdot BET(P | a_P, b_P). \end{cases}$$

Because of the hierarchy of the probabilistic model of FIG. 4, account being taken also of the above marginalized joint law and its parameters independent from $M_0$, it is easily shown that the conditional posterior probability law followed by the parameter $M_0$ takes the following form:

$$p(M_0|\underline{Y}, \epsilon, \underline{q}, P) = N(\underline{Y}|c(M_0 \cdot \underline{q}, \underline{z}) * \underline{h}, \epsilon \cdot I_T) \cdot GAM(M_0|k_m, T_m).$$

It is shown in the same way that:

$$p(\underline{q} | \underline{Y}, \epsilon, M_0, P) = N(\underline{Y} | c(M_0 \cdot \underline{q}, z) * \underline{h}, \epsilon \cdot I_T) \cdot \left(P^{\Omega(\underline{q}, 1)} \cdot (1-P)^{\Omega(\underline{q}, 0)}\right),$$

$$p(\epsilon | \underline{Y}, M_0, \underline{q}, P) = N(\underline{Y} | c(M_0 \cdot \underline{q}, z) * \underline{h}, \epsilon \cdot I_T) \cdot IGAM(\epsilon | k_\epsilon, T_\epsilon)$$
$$= IGAM\left(\epsilon \left| \left(k_\epsilon + \frac{T}{2}\right), (T_\epsilon + 0,5 \cdot \|\underline{Y} - c(M_0 \cdot \underline{q}, z) * \underline{h}\|^2)\right.\right),$$

and $$p(P | \underline{Y}, \epsilon, M_0, \underline{q}) = \left(P^{\Omega(\underline{q}, 1)} \cdot (1-P)^{\Omega(\underline{q}, 0)}\right) \cdot BET(P | a_P, b_P)$$
$$= BET(P | (a_P + \Omega(\underline{q}, 1)), (b_P + \Omega(\underline{q}, 0))).$$

The above equations show that the conditional posterior probability laws of the unknown parameters $\epsilon$, $M_0$, $\underline{q}$ and P can be expressed analytically and used in the same way as in the first embodiment.

In the light of the above, the molecular mass parameter estimation method illustrated in FIG. 3, including the first main conjoint estimation phase 100, the second main reconstruction phase 200 and the optional prior external calibration phase 300, applies in the same way.

In particular, during the initialization step 104, the random variables $\epsilon$, $M_0$, $\underline{q}$ and P are each initialized by the processor 28 to a first value $\epsilon^{(0)}$, $M_0^{(0)}$, $\underline{q}^{(0)}$ and $P^{(0)}$.

The processor 28 then executes, by applying a Markov chain Monte-Carlo algorithm to an index k varying from 1 to kmax, the Gibbs sampling loop 106 of each of the random variables initialized with a view to their respective conditional posterior probability laws as expressed analytically.

More precisely, for k varying from 1 to kmax, the loop 106 comprises the following successive samplings:
generating a sample $\epsilon^{(k)}$ from the posterior law $p(\epsilon|\underline{Y}, M_0^{(k-1)}, \underline{q}^{(k-1)}, P^{(k-1)})$,
defining the neighborhood of the parameter $M_0$ from the value $M_0^{(k-1)}$,
generating a sample $M_0^{(k)}$, in the neighborhood of $M_0^{(k-1)}$ from the posterior law $p(M_0|\underline{Y}, \epsilon^{(k)}, \underline{q}^{(k-1)}, P^{(k-1)})$,
defining the neighborhood of the parameter $\underline{q}$ from the value $\underline{q}^{(k-1)}$,
generating a sample $\underline{q}^{(k)}$, in the neighborhood of $\underline{q}^{(k-1)}$ from the posterior law $p(\underline{q}|\underline{Y}, \epsilon^{(k)}, M_0^{(k)}, P^{(k-1)})$, and
generating a sample $P^{(k)}$ from the posterior law $p(P|\underline{Y}, \epsilon^{(k)}, M_0^{(k)}, \underline{q}^{(k)})$.

In addition, at each iteration, the marginalized joint law is estimated and its value is stored in memory with the current values $\epsilon^{(k)}$, $M_0^{(k)}$, $\underline{q}^{(k)}$, $P^{(k)}$.

The estimation step 108 supplies the estimated values $\hat{\epsilon}$, $\hat{M}_0$, $\hat{q}$ and $\hat{P}$ for each of the unknown parameters $\epsilon$, $M_0$, $\underline{q}$ and P. An estimated value $\hat{\underline{m}} = \hat{M}_0 \cdot \hat{q}$ for the parameter $\underline{m}$ is directly derived therefrom.

The following spectrum reconstruction phase 200 is also unchanged.

Finally, it should be noted that a variant with internal calibration cannot be effected in this second embodiment since it is taken as a hypothesis that the analyzed sample includes only components having the same single molecular mass. Such a calibration would assimilate the model to that of a third embodiment that will now be detailed.

In this third embodiment, in which it is assumed that the molecules of the sample E have a discrete plurality of molecular masses, the parameter $\underline{m}$ can be refined by introducing the theoretical parameter q mentioned in the first two embodiments. Unlike a continuous distribution of masses, it is assumed that the molecules of the sample E* are grouped together in classes, each molecule in a given class having the same mass as all the other molecules in the same class. The number of these classes is denoted C. The parameter $\underline{m}$ can then be expressed in the form $\underline{m}=M(\underline{Cq})\cdot q$ where $\underline{Cq}$ is a vector with T components, each of its components indicating the index i, $1 \leq i \leq C$, of a class and where $M(\underline{Cq})$ is a vector with T components, each of its components indicating the mass associated with the class indicated in the corresponding component of the vector $\underline{Cq}$. To pass from the class succession vector $\underline{Cq}$ to the masse succession vector $M(\underline{Cq})$ a vectorial parameter M with C independent components corresponding respectively to the C classes is introduced, each of its components indicating the mass associated with the corresponding class.

It is also necessary to introduce another parameter Cp, a vector with C components, each component of this vector indicating the probability of the corresponding class, the vector therefore finally indicating the distribution of the C classes in terms of probability.

In this new model chosen, the vectorial parameter M is "uncertain" and its C independent components $M_i$, $1 \leq i \leq C$, are modeled according to a predetermined prior probability law, for example a gamma law $GAM(M_i|k_m, T_m)$ of form $k_m$ and intensity $T_m$, these last two parameters representing the prior knowledge on the molecular mass parameter denoted $\theta_m$.

Also in this new model chosen, the integer parameter C is "uncertain" and is modeled according to a predetermined prior probability law, for example a Poisson law of parameter $\lambda_C$, this parameter representing the prior knowledge on the parameter C denoted $\theta_C$. In a variant, the parameter C could be known and its prior probability law represented by a Dirac distribution centered on the known value.

In this new model chosen also, the vectorial parameter $\underline{Cq}$ is "uncertain", its components are discrete values lying between 1 and C and the probability for any one of its components to be equal to i, $1 \leq i \leq C$, is equal to the value of the $i^{th}$ component of Cp.

In this new model chosen also, the vectorial parameter Cp is "uncertain" and is modeled on a predetermined prior probability law, for example a Dirichlet law $D(Cp, \{a_{Cp}, \ldots, a_{Cp}\})$ with form parameters all equal to a value $a_{Cp}$, this common value representing the prior knowledge on the parameter Cp denoted $\theta_{Cp}$.

Figure 5:
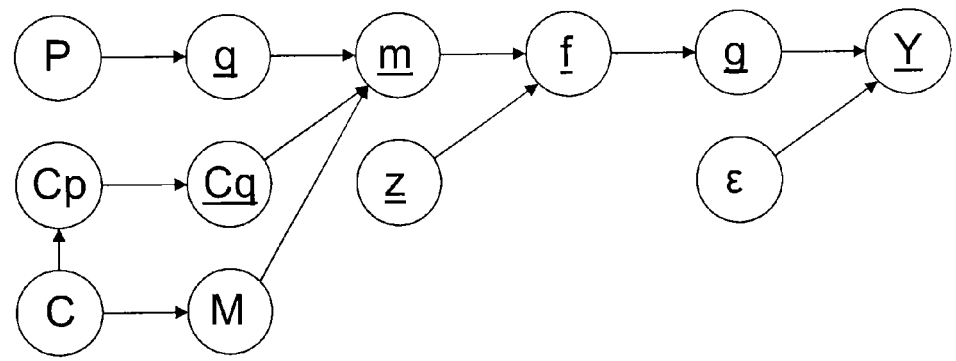
FIG. 5 illustrates a third analytical modeling of a processing chain of the device of FIG. 1 according to a third embodiment of the invention.

As illustrated in FIG. 5 in the context of the third embodiment, the "uncertain" parameters of the new model are defined as having a probabilistic dependency relationship with each other, leading to a hierarchical global probabilistic model.

Thus the parameter q is dependent on the parameter P, the parameter $\underline{m}$ dependent on the parameter q, the parameter $\underline{Cq}$ and the parameter M as defined previously by the equation $\underline{m}=M(\underline{Cq})\cdot q$, the parameter $\underline{Cq}$ dependent on the parameter Cp by definition, the parameters M and Cp dependent on the parameter C which defines their vectorial size, the function $\underline{f}$ dependent on the parameters $\underline{m}$ and $\underline{z}$, the function $\underline{g}$ dependent on the function $\underline{f}$ and the observed signal $\underline{Y}$ dependent on the function $\underline{g}$ and the noise parameter $\varepsilon$.

Consequently, as can be seen in FIG. 5, at a first hierarchy level of the probabilistic model, the observed signal $\underline{Y}$ depends solely on the random variables $\underline{g}$ and $\varepsilon$, the latter being defined by the nature of its prior probabilistic model and the prior knowledge $\theta_\varepsilon$. At a second hierarchy level of the probabilistic model, the random variable $\underline{g}$ depends solely on the random variable $\underline{f}$. At a third hierarchy level of the probabilistic model, the random variable $\underline{f}$ depends solely on the random variables $\underline{m}$ and $\underline{z}$, the latter being in fact known by virtue of the presence of the detection device 24. At a fourth hierarchy level of the probabilistic model, the random variable $\underline{m}$ depends solely on the random variables q, $\underline{Cq}$ and M, the latter being defined by the nature of its prior probabilistic model and the prior knowledge $\theta_m$. At a fifth hierarchy level of the probabilistic model, the random variable q depends solely on the random variable P, the latter being defined by the nature of its prior probabilistic model and the prior knowledge $\theta_P$. At the fifth hierarchy level of the probabilistic model also, the random variable $\underline{Cq}$ depends solely on the random variable Cp, the latter being defined by the nature of its prior probabilistic model and the prior knowledge $\theta_{Cp}$. At the fifth hierarchy level of the probabilistic model also, the random variable M depends only on the random variable C, the latter being defined by the nature of its prior probabilistic model and the prior knowledge $\theta_C$. Finally, at a sixth hierarchy level of the probabilistic model also, the random variable Cp depends only on the random variable C.

On the basis of this hierarchical probabilistic model, the molecular mass parameter estimation method described previously applies in a similar fashion for an estimation of the parameter $\underline{m}$ and the mass spectrum Sp.

According to the first inversion phase of this method, the estimation of the parameter $\underline{m}$ is done conjointly with the estimation of all the random variables $\varepsilon$, $\underline{g}$, $\underline{f}$, $\underline{z}$, $\underline{m}$, M, $\underline{Cq}$, Cp, C, q and P by application of an estimator to the joint posterior probability law of these random variables in the light of the observation $\underline{Y}$ or, in an equivalent fashion, to the joint probability law of these random variables and the observation $\underline{Y}$.

In particular, the joint probability law of the random variables and the observation is developed in the following way, by means of the hierarchical model of FIG. 5:

$$p(\underline{Y}, \varepsilon, \underline{g}, \underline{f}, z, \underline{m}, q, P, M, \underline{Cq}, Cp, C) = \begin{cases} p(\underline{Y}|\varepsilon, \underline{g}) \cdot p(\varepsilon|\theta_\varepsilon) \cdot p(\underline{g}|\underline{f}) \cdot p(\underline{f}|z, \underline{m}) \cdot p(z|\theta_z) \cdot \\ p(\underline{m}|M, \underline{Cq}, q) \cdot p(q|P) \cdot p(P|\theta_P) \cdot p(\underline{Cq}|Cp) \cdot \\ p(M|\theta_m, C) \cdot p(Cp|\theta_{Cp}, C) \cdot p(C|\theta_C) \end{cases}$$

In the light of the deterministic dependencies between some of these parameters and prior probability laws chosen for others (as indicated previously for the parameters $\varepsilon$, M, q, P, $\underline{Cq}$, Cp, C), this knowledge being able in particular to be acquired by an external calibration, the joint law of the random variables and the observation is easily marginalized to:

$$p(\underline{Y}, \varepsilon, M, q, P, \underline{Cq}, Cp, C) = \begin{cases} N(\underline{Y}|c(M \cdot (\underline{Cq}) \cdot q, z) * \underline{h}, \varepsilon \cdot I_T) \cdot IGAM(\varepsilon|k_\varepsilon, T_\varepsilon) \cdot \\ \prod_{i=1}^{C} GAM(M_i|k_m, T_m) \cdot \left(P^{\Omega(q,1)} \cdot (1-P)^{\Omega(q,0)}\right) \cdot \\ BET(P|a_P, b_P) \cdot \prod_{i=1}^{C} Cp_i^{\Omega(Cq,i)} \cdot D(Cp, a_{Cp}, \ldots, a_{Cp}) \cdot e^{-\lambda_C} \cdot \frac{\lambda_C}{C!}. \end{cases}$$

Because of the hierarchy of the probabilistic model of FIG. 5, because also of the above marginalized joint law and its parameters independent from M, it is easily shown that the conditional posterior probability law followed by the parameter M takes the following form:

$$p(M \mid \underline{Y}, \varepsilon, \underline{q}, P, \underline{Cq}, Cp, C) =$$
$$N(\underline{Y} \mid c(M \cdot (\underline{Cq}) \cdot \underline{q}, z) * \underline{h}, \varepsilon \cdot I_T) \cdot \prod_{i=1}^{C} GAM(M_i \mid k_m, T_m).$$

It is shown in the same way that:

$$p(\underline{q} \mid \underline{Y}, \varepsilon, M, P, \underline{Cq}, Cp, C) =$$
$$N(\underline{Y} \mid c(M(\underline{Cq}) \cdot \underline{q}, z) * \underline{h}, \varepsilon \cdot I_T) \cdot \left( P^{\Omega(\underline{q},1)} \cdot (1-P)^{\Omega(\underline{q},0)} \right),$$

$$p(\varepsilon \mid \underline{Y}, M, \underline{q}, P, \underline{Cq}, Cp, C) = N(\underline{Y} \mid c(M(\underline{Cq}) \cdot \underline{q}, z) * \underline{h}, \varepsilon \cdot I_T) \cdot$$
$$IGAM(\varepsilon \mid k_\varepsilon, T_\varepsilon)$$
$$= IGAM \left( \begin{array}{c} \varepsilon \mid \left( k_\varepsilon + \dfrac{T}{2} \right), \\ \left( T_\varepsilon + 0, 5 \cdot \right. \\ \left. \|\underline{Y} - c(M(\underline{Cq}) \cdot \underline{q}, z) * \underline{h}\|^2 \right) \end{array} \right),$$

$$p(P \mid \underline{Y}, \varepsilon, M, \underline{q}, \underline{Cq}, Cp, C) = \left( P^{\Omega(\underline{q},1)} \cdot (1-P)^{\Omega(\underline{q},0)} \right) \cdot BET(P \mid a_P, b_P)$$
$$= BET(P \mid (a_P + \Omega(\underline{q}, 1)), (b_P + \Omega(\underline{q}, 0))),$$

$$p(\underline{Cq} \mid \underline{Y}, \varepsilon, M, \underline{q}, P, Cp, C) =$$
$$N(\underline{Y} \mid c(M \cdot (\underline{Cq}) \cdot \underline{q}, z) * \underline{h}, \varepsilon \cdot I_T) \cdot \prod_{i=1}^{C} Cp_i^{\Omega(\underline{Cq},i)},$$

$$p(Cp \mid \underline{Y}, \varepsilon, M, \underline{q}, P, \underline{Cq}, C) = \prod_{i=1}^{T} Cq_i^{\Omega(\underline{Cq},i)} \cdot D(Cp, a_{Cp}, \ldots, a_{Cp})$$
$$= D(Cp, (a_{Cp} + \Omega(\underline{q}, 1)), \ldots, (a_{Cp} + \Omega(\underline{q}, C)))$$

The above equations show that the conditional posterior probability laws of the unknown parameters ε, M, q, P, Cq and Cp can be expressed analytically since they are proportional to products of prior distributions or probabilities that can either be modeled or defined by learning.

More precisely, the posterior probability for the noise parameter ε follows a gamma-inverse law, as in the previous embodiments, so that the sampling of this parameter can be done simply and conventionally in the context of an iterative Gibbs sampling method.

Likewise, the posterior probability for the parameter P follows a beta law, as in the previous embodiments, so that the sampling of this parameter can be done simply and conventionally in the context of an iterative Gibbs sampling method.

The posterior probability for the parameter M is expressed in the form of a product of a normal law and gamma laws so that it is necessary to use a random walk sampling technique, as in the previous embodiments for $\mu$ and $M_0$. Such a sampling technique requires defining, at each iteration, a neighborhood of the parameter M as estimated at the previous iteration in order to proceed with the drawing of a new value. This neighborhood will be defined as in the previous embodiments for $\mu$ and $M_0$.

The posterior probability for the parameter q is expressed in the form of the product of a normal law and a Bernoulli law so that it will be necessary to use a random walk sampling technique, as in the previous embodiments. Such a sampling technique requires defining at each iteration a neighborhood of the parameter q as estimated at the previous iteration in order to proceed with the drawing of a new value. This neighborhood will be defined as in the previous embodiments.

The posterior probability for the parameter Cq is expressed in the form of the product of a normal law and a variable number of prior probabilities. This posterior probability does not have a simple expression, so that it will be necessary to use a random walk sampling technique, such as the random walk Metropolis-Hastings (RWMH) algorithm or an algorithm approximating this, make it necessary to define a neighborhood of the parameter Cq. This parameter being by hypothesis a vector with discrete values, a particular concept of neighborhood will now be defined.

According to a first variant, a process that proposes at each iteration as many neighbors as there are classes is iterated on the components of the vector Cq. Thus, at the $k^{th}$ iteration of this process, the $k^{th}$ component of Cq can be equal to all the integers between 1 and C: it will have C−1 selectable neighbors (in addition, optionally, to the current value) during sampling.

According to a second variant, advantageously for saving computing time in the case of a high number of classes, it suffices to define a single neighbor for the $k^{th}$ component of Cq, drawing at random from the C−1 possible values other than the current value: the $k^{th}$ component will then have 1 selectable neighbor in addition to the current value during sampling.

The posterior probability for the parameter Cp follows a Dirichlet law so that sampling of this parameter can be done simply and conventionally in the context of an iterative Gibbs sampling method.

On the other hand, there is no usable analytic expression of the posterior probability for the parameter C so that its sampling must be done according to a particular method, in coordination with the sampling of other unknown parameters.

Figure 6:
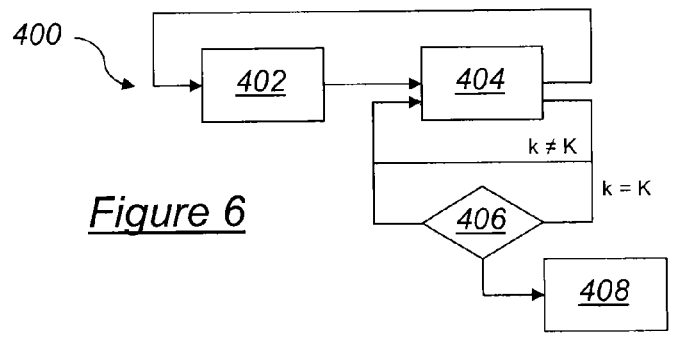
FIG. 6 illustrates the detail of a step of the estimation method of FIG. 3, according to the third embodiment of the invention.

In light of the above, the molecular mass parameter estimation method illustrated in FIG. 3, including the first main conjoint estimation phase 100, the second main reconstruction phase 200 and the optional prior external calibration phase 300, applies in the same way, except for the Gibbs sampling loop 106, which must be replaced by a more complex sampling loop 400, suited to the particular sampling of the parameter C and illustrated in FIG. 6.

Thus, after having initialized each of the random variables ε, M, q, P, Cq, Cp and C to a first value $\varepsilon^{(0)}$, $M^{(0)}$, $q^{(0)}$, $P^{(0)}$, $Cq^{(0)}$, $Cp^{(0)}$ and $C^{(0)}$ during the initialization step 104 and after having initialized the value of the marginalized joint law, the processor 28 executes the sampling loop 400.

During a first step 402 of this sampling loop 400, a sample of C is generated according to its prior probability law around its current value, the last values of the other unknown parameters and the last value of the marginalized joint law being stored in memory.

If this prior probability law is a Poisson law as indicated previously, the sampling 402 of the parameter C consists of adding or removing a class and:
  if a class is removed, merging the two classes closest in terms of masses,
  if a class is added, creating a new class the mass of which is drawn according to the a priori law of the parameter M.

It will be noted that it is possible, optionally, to favor (or respectively penalize) the removal of a class if there exist (or respectively if there do not exist) two classes very close in terms of masses.

Next, during a Gibbs sampling step 404, the other parameters ε, M, q, P, Cq and Cp are sampled.

More precisely, for k varying from 1 to no more than kmax, the step 404 comprises the following successive samplings:

generating a sample $\epsilon^{(k)}$ from the posterior law $p(\epsilon|\underline{Y}, \underline{q}^{(k-1)}, P^{(k-1)}, M^{(k-1)}, \underline{Cq}^{(k-1)}, Cp^{(k-1)})$, defining the neighborhood of the parameter $\underline{q}$ from the value $\underline{q}^{(k-1)}$, generating a sample $\underline{q}^{(k)}$ in the neighborhood of $\underline{q}^{(k-1)}$ from the posterior law $p(\underline{q}|\underline{Y}, \epsilon(k), P^{(k-1)}, M^{(k)}, \underline{Cq}^{(k-1)}, Cp^{(k-1)})$ generating a sample $P^{(k)}$ from the posterior law $p(P|\underline{Y}, \epsilon^{(k)}, \underline{q}^{(k)}, M^{(k-1)}, \underline{Cq}^{(k-1)}, Cp^{(k-1)})$, defining the neighborhood of the parameter M from the value $M^{(k-1)}$, generating a sample $M^{(k)}$ in the neighborhood of $M^{(k-1)}$ from the posterior law $p(M|\underline{Y}, \epsilon^{(k)}, \underline{q}^{(k)}, P^{(k)}, \underline{Cq}^{(k-1)}, Cp^{(k-1)})$, defining the neighborhood of the parameter $\underline{Cq}$ from the value $\underline{Cq}^{(k-1)}$, generating a sample $\underline{Cq}^{(k)}$ in the neighborhood of $\underline{Cq}^{(k-1)}$ from the posterior law $p(\underline{Cq}|\underline{Y}, \epsilon^{(k)}, \underline{q}^{(k)}, P^{(k)}, M^{(k)}, Cp^{(k-1)})$, and generating a sample $Cp^{(k)}$ from the posterior law $p(Cp|\underline{Y}, \epsilon^{(k)}, \underline{q}^{(k)}, P^{(k)}, M^{(k)}, \underline{Cq}^{(k)})$.

In addition, at each iteration, the marginalized joint law is estimated and its value is stored in memory with the current values $\epsilon^{(k)}$, $\underline{q}^{(k)}$, $P^{(k)}$, $M^{(k)}$, $\underline{Cq}^{(k)}$ and $Cp^{(k)}$.

At the end of a predetermined number of K iterations, $1 \leq K \leq kmax$, a test 406 is executed on the current value of the marginalized joint law. If this current value remains below the value stored in memory at step 402, then step 404 is interrupted and a step 408 is passed to during which the last values of parameters stored in the memory at step 402 are restored with a probability dependent on the values of the probability of the marginalized joint law before and after the sampling 402 of the parameter C. Step 408 ends the sampling loop 400 and is followed by step 108. If the current value of the marginalized joint law tested at step 406 is higher than the last value stored in memory at step 402, then step 404 is carried to its end and followed by a return to step 402.

The estimation step 108 supplies the estimated values $\hat{\epsilon}$, $\hat{\underline{q}}$, $\hat{P}$, $\hat{M}$, $\hat{\underline{Cq}}$, $\hat{Cp}$ and $\hat{C}$ for each of the unknown parameters $\epsilon$, $\underline{q}$, P, M, $\underline{Cq}$, Cp and C. An estimated value $\hat{\underline{m}} = \hat{M}(\hat{\underline{Cq}}) \cdot \hat{\underline{q}}$ is derived from this directly for the parameter $\underline{m}$.

The following spectrum reconstruction phase 200 is unchanged.

In a variant of the third embodiment that has just been described, an internal calibration can be carried out by incorporating in the sample E, at step 102, a sample E* of known marking weighted components.

A first consequence of such an internal calibration carried out during the measurement step 102 is to add a prior knowledge to at least some of the parameters of the processing chain 12. In particular, the prior law on the number C of classes becomes necessarily zero below a known minimum according to the sample of weighted components E*: this minimum corresponds to the number of classes of weighted components. In addition, this also gives rise to knowledge on the vector M, which must contain the corresponding indications on the masses of the weighted components of the sample E*. It is then necessary to separate the vector M into two sub-vectors: a vector $M_i$ of the components of the sample E, called into question at each sampling, and a vector $M_c$ of the weighted components of the sample E*, never called into question.

Another consequence concerns step 206, the inverse of the gain used for weighting the histogram of the parameter $\underline{m}$ not being known a priori but estimated by the processing device 14 by means of the internal calibration.

It is clear that a method such as the one described previously, implemented by the estimation device 10, makes it possible, by virtue of a fine probabilistic modeling of the processing chain 12, to provide a reliable estimation of a molecular mass parameter of components of a sample to be analyzed. In particular, this method excels in evaluating individually the masses of the components of the sample, which the conventional analysis methods do less well.

Concrete applications of this method comprise in particular the detection of cancerous markers (in this case the components are proteins) in a biological blood or urine sample.

It will also be noted that the invention is not limited to the embodiments described previously. It will be clear in fact to a person skilled in the art that various modifications can be made to the embodiment described above in the light of the teaching that has just been disclosed to him.

In particular, the components of interest are not necessarily proteins, but may more generally be molecules or molecular assemblies for biological or chemical analysis.

In a variant also, probabilistic models with other parameters may be chosen other than those presented in relation to FIGS. 2, 4 and 5. In particular, in the third embodiment, by changing the definition of the vectorial parameter $\underline{q}$ so that it itself includes information on the classes, it becomes optionally possible to dispense with the parameters $\underline{Cq}$ and Cp.

In a variant also, it is possible to call into question the hypothesis of the gains Ge, Gf, Gc independent of the mass of the molecules in a relatively simple manner: if several concentration references are available, whether during external or internal calibration, it is possible to estimate each of the assumed gains for each of the references, then interpolate the gain values obtained (by splines, for example). The resulting curve can be inverted in order to serve to multiply the histogram of $\underline{m}$ during step 206.

In a variant also, when a Gibbs sampling loop is executed, whether during step 106 or during step 404, it is possible to call into question the result of each iteration. For example, during the estimation of the marginalized joint law at the end of iteration, by comparing this new estimation with the previous value, if the value is lower, the new set of parameters is accepted with a probability equal to the ratio of the new probability to the old probability. It is also possible to envisage a variant according to which the parameters are systematically accepted during a sampling iteration and where the set of parameters is called into question at the end of the iteration.

In a variant also, in the first and third embodiments, in which the parameters g and M are vectors, the Gibbs sampling may, instead of taking place globally over the whole of the vector, be done component by component, either from the first to the last, or in another predetermined order, or by running through the vectorial components in a random order so that a predetermined travel direction has no influence on the results of the sampling.

In a variant also, an adsorption merger process can be undertaken for certain components of the parameter g, for example by stochastic election of the components concerned. During such a merger process, each pair of sufficiently close adsorptions are merged. In addition, it is possible:

in the first embodiment, to replace the mass associated (in the vector g) with the new adsorption created by the sum of the two old masses estimated for the two merged adsorptions, in the second and third embodiments, to increase respectively $M_0$ and M by certain quantity, for example the ratio between the number of adsorptions and the number of components from which 1 is deducted in the parameter q.

More generally, in the following claims, the terms used must not be interpreted as limiting the claims to the embodiments disclosed in the present description, but must be interpreted so as to include therein all the equivalents that the claims aim to cover because of their wording and the prediction of which is within the capability of a person skilled in the art applying his general knowledge to the use of the teaching that has just been disclosed to him.

The invention claimed is:

1. A method for estimating a molecular mass parameter in a sample that includes at least one component of a given molecular mass and having an adsorption, comprising the following steps:
    passing the sample through a processing chain comprising a mass spectrometer with a Micro Electro Mechanical System (MEMS) or Nano Electro Mechanical System (NEMS) electromechanical sensor, in order to count a number of successive detections of said component's adsorption by way of progressive changes in an operating frequency of the sensor;
    from said passing, obtaining a signal from said mass spectrometer representing the molecular mass parameter; and
    estimating the molecular mass parameter with a signal processing device including a programmed sequence of instructions,
    wherein the molecular mass parameter is defined based on a parameter of time distribution of successive detections, by the MEMS or NEMS electromechanical sensor, of the adsorption of said component, and wherein the estimation of the molecular mass parameter by the signal processing device is made by Bayesian inference, based on a direct analytical modeling of said signal according to the molecular mass parameter and to technical parameters of the processing chain comprising at least one technical parameter of the MEMS or NEMS electromechanical sensor.

2. A method for estimating at least one molecular mass parameter according to claim 1, wherein the analytical modeling comprises a parameter that represents detection instants at which the electromechanical sensor detects the adsorption of said component, and wherein the molecular mass parameter is defined from said parameter that represents the detection instants.

3. A method for estimating at least one molecular mass parameter according to claim 2, wherein the parameter that represents the detection instants is a vector or of a list of parameters of each component detection.

4. A method for estimating at least one molecular mass parameter according to claim 3, wherein:
    the parameter that represents the detection instants is a vector with binary components, one of the binary values, A, indicating the detection of an adsorption,
    at each iteration of a sampling loop, a sample of this parameter is calculated in a neighborhood of the sample calculated at the previous iteration,
    the neighborhood of a current sample of this parameter is defined in the following way: any sample comprising a component with A plus or minus, a component with A shifted, or a component A grouping together two components with successive As of the current sample.

5. A method for estimating at least one molecular mass parameter according to claim 1, further comprising a step for detecting the adsorption sites of components on the MEMS or NEMS electromechanical sensor, wherein the analytical modeling further comprises a parameter of time distribution of said adsorption sites and a deterministic function that returns a value of drop in frequency for each pair of values for a mass of adsorbed component and for a corresponding adsorption site.

6. A method for estimating at least one molecular mass parameter according to claim 1, wherein at least two of the molecular mass parameters and the processing chain parameters according to which the direct analytical modeling of said signal is defined have a probabilistic dependency relationship with each other, and wherein the signal processing by Bayesian inference is further carried out based on a modeling by a conditional prior probability law of this dependency.

7. A method for estimating at least one molecular mass parameter according to claim 1, wherein the step of estimating the molecular mass parameter comprises, by approximation of the joint posterior probability law of a parameter linked to the molecular mass parameter and the technical parameters of the processing chain conditionally to the signal obtained with a stochastic sampling algorithm:
    a sampling loop for sampling these parameters, that supplies sampled values of these parameters, and
    an estimation of the molecular mass parameter calculated from the sampled values supplied.

8. A method for estimating at least one molecular mass parameter according to claim 7, wherein:
    at each iteration of the sampling loop, a joint probability of at least all the sampled parameters is estimated, and
    the estimation of the molecular mass parameter is done, conjointly with that of the sampled parameters, on the basis of the successive values of said joint probability.

9. A method for estimating at least one molecular mass parameter according to claim 7, wherein the molecular mass parameter is a mass spectrum that relates to at least one component the mass of which forms part of the parameters processed by the sampling loop and is one of the elements of the group consisting of a single molecular mass, a discrete plurality of molecular masses and a continuous distribution of masses.

10. A method for estimating at least one molecular mass parameter according to claim 1, wherein the molecular mass parameter relates to proteins and the sample comprises one of the elements of the group consisting of blood, plasma, urine, biological fluid and lysate of a biological sample.

11. A device for estimating a molecular mass parameter in a sample, comprising:
    a chain for processing the sample, comprising a mass spectrometer with a Micro Electro Mechanical System (MEMS) or Nano Electro Mechanical System (NEMS) electromechanical sensor, designed for supplying a signal representing the molecular mass parameter;
    a signal processing device designed to apply, in combination with the processing chain, a molecular mass parameter estimation method according to claim 1,
    wherein the molecular mass parameter is defined on the basis of a parameter of time distribution of successive detections, by the MEMS or NEMS electromechanical sensor, of adsorbed components' masses.

* * * * *